United States Patent [19]

Lee

[11] Patent Number: 4,613,675

[45] Date of Patent: Sep. 23, 1986

[54] PHOSPHORUS CONTAINING 1-CYCLOHEXENE-1,2-DICARBOXAMIDES

[75] Inventor: Shy-Fuh Lee, Sunnyvale, Calif.

[73] Assignee: Sandoz Ltd., Basel, Switzerland

[21] Appl. No.: 677,113

[22] Filed: Nov. 30, 1984

[51] Int. Cl.[4] .......................... C07F 9/32; A01N 57/02
[52] U.S. Cl. ........................................ 558/170; 71/86; 71/87
[58] Field of Search ........................................ 260/942

[56] References Cited

U.S. PATENT DOCUMENTS 4,560,752 12/1985 Lee ........................................ 260/942

Primary Examiner—Anton H. Sutto
Attorney, Agent, or Firm—Jacqueline S. Larson; Hana Dolezalova

[57] ABSTRACT

Substituted 1-cyclohexene-1,2-dicarboxamides, synthesis thereof, intermediates therefor, and the use of said compounds for the control of weeds.

13 Claims, No Drawings

PHOSPHORUS CONTAINING 1-CYCLOHEXENE-1,2-DICARBOXAMIDES

The present invention relates to novel substituted 1-cyclohexene-1,2-dicarboxamides, synthesis thereof, intermediates therefor, and the use of said novel compounds for the control of weeds.

More particularly, the novel compounds of the present invention are represented by the following formula (A):

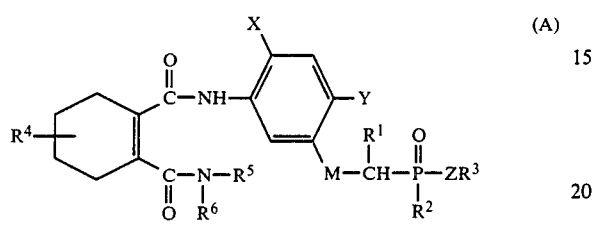

wherein,

M is oxygen, sulfur, sulfinyl, sulfonyl or N—R;
each of X and Y is independently hydrogen or halogen;
Z is O;
each of R, R' and $R^1$ is independently hydrogen or lower alkyl;
$R^2$ is lower alkyl;
$R^3$ lower alkyl, alkoxyalkyl, or alkoxycarbonylalkyl;
$R^4$ is hydrogen;
each of $R^5$ is lower alkyl, cycloalkyl or alkoxyalkyl; and $R^6$ is hydrogen or lower alkyl.

In the description and claims hereinafter, each of $R$-$R^6$, R', M, X, Y and Z is as defined above, unless otherwise specified.

The compounds of the present invention of formula (A) can be synthesized as outlined below, by the reaction of an amino compound of formula (IV) with 3,4,5,6-tetrahydrophthalic anhydride, in the presence of an acid such as acetic acid. The resulting tetrahydrophthalimide (B) is then reacted with an amine (V) at room temperature or below.

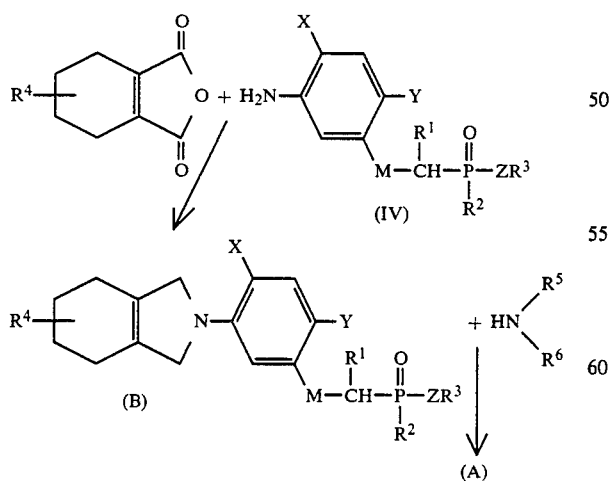

The compounds of formula (IV) where M is oxygen, Z is oxygen, $R^3$ is lower alkyl and X is other than fluoro can be synthesized as outlined below:

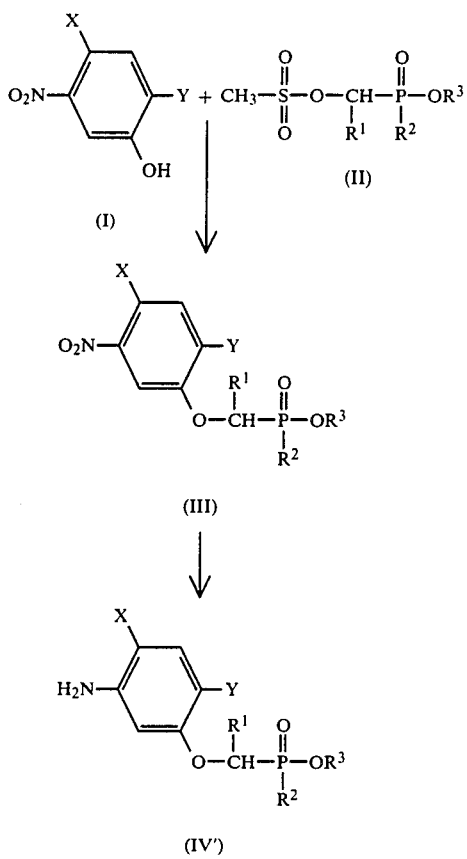

In the above synthesis, a nitrophenol (I) is reacted with a sulfonate (II) (where $R^2$=lower alkyl) to give a nitrophenoxyalkylphosphinate (III), which is then hydrogenated to the corresponding amino compound (IV').

The compounds of formula (IV') where $R^2$ is lower alkoxy are prepared by the reaction of a nitrophenol of formula (I) with an alcohol of formula (XIV) (where $R^2$=lower alkoxy) to give a nitrophenoxyalkylphosphonate (III), which is then hydrogenated following the procedure of S. Bittner and Y. Assaf, Chem. Ind. (London) (6):(281) (1975).

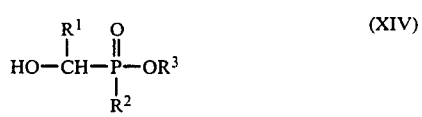

To prepare compounds of formula (IV') where the values of X include fluoro, an aminophenol of formula (XV) is reacted with either a sulfonate of formula (II) or an alcohol of formula (XIV) to give directly the corresponding aminophenoxy compound (IV').

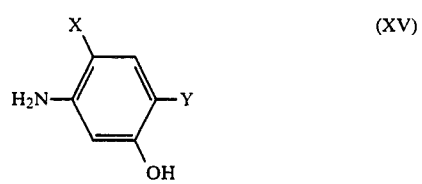

The compounds of formula (IV) where M is N—R, Z is oxygen and $R^3$ is lower alkyl can be synthesized as outlined below:

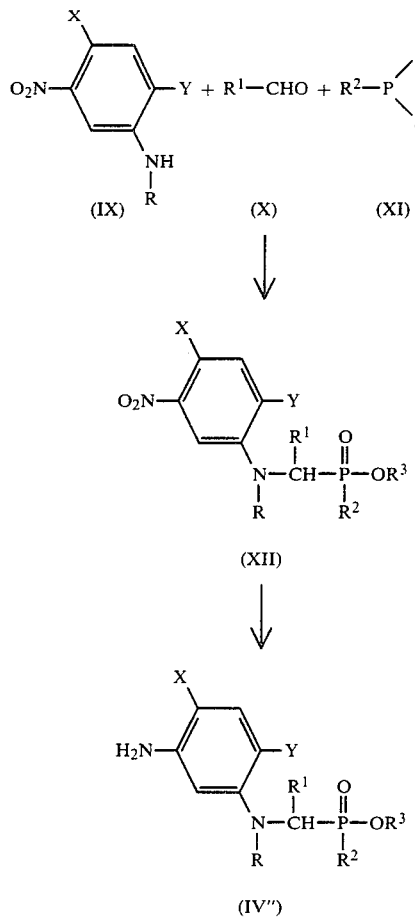

In the above synthesis, a nitroaniline (IX) is reacted with an aldehyde (X) [where $R^1=H$, $(CH_2O)_n$ is used] and a phosphite (where $R^2$=alkoxy) or phosphonite (where $R^2$=alkyl) (XI) in the presence of $BF_3$/ether and a solvent such as toluene to give a nitrophenylphosphonate or phosphinate (XII), which is then hydrogenated to the corresponding amino compound (IV''').

To prepare compounds of formula (IV) where $R^3$ is other than lower alkyl or where Z is sulfur or amino, a compound of formula (III) (where $R^3$ is lower alkyl) is halogenated by reaction with, for example, thionyl chloride or oxalyl chloride, and the resulting halophosphinate or phosphonate (VI; Q is $NO_2$, M is oxygen or N—R and XX is halo) is reacted with a compound of the formula $R^3$—ZH. The resulting compound is then hydrogenated to the corresponding amino compound (IV) (where M is oxygen or N—R).

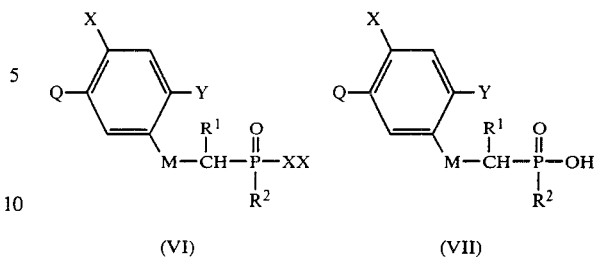

In an alternative method for preparing compounds of formula (IV) where $R^3$ is alkoxycarbonylalkyl and M is oxygen or N—R, formula (VI) is hydrolyzed to the corresponding phosphinic or phosphonic acid (VII). A compound of formula (VII) is then reacted with a halide of formula (VIII) to give a compound of formula (XVI) ($R^7$ is hydrogen or lower alkyl, and $R^8$ is lower alkyl). Where Q is $NO_2$, the resulting compound is then hydrogenated to the corresponding amino compound.

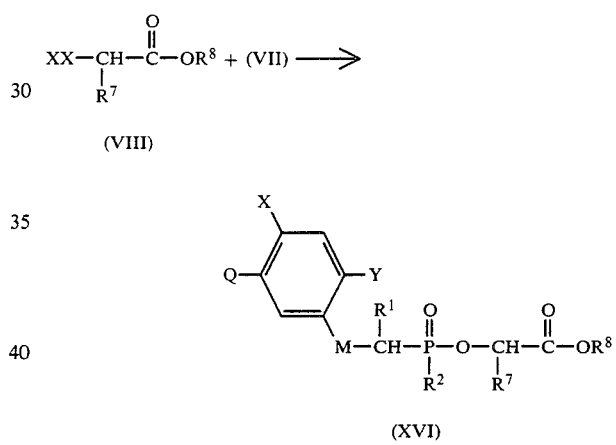

The compounds of formula (IV) where M is sulfur can be prepared as outlined below:

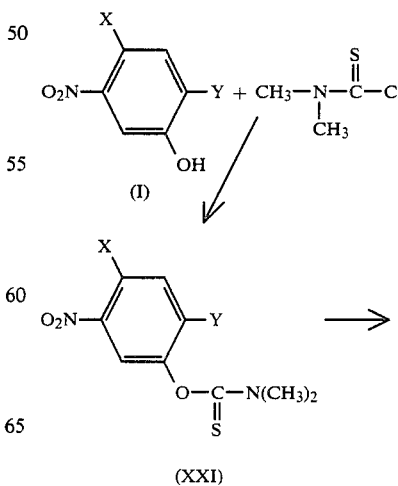

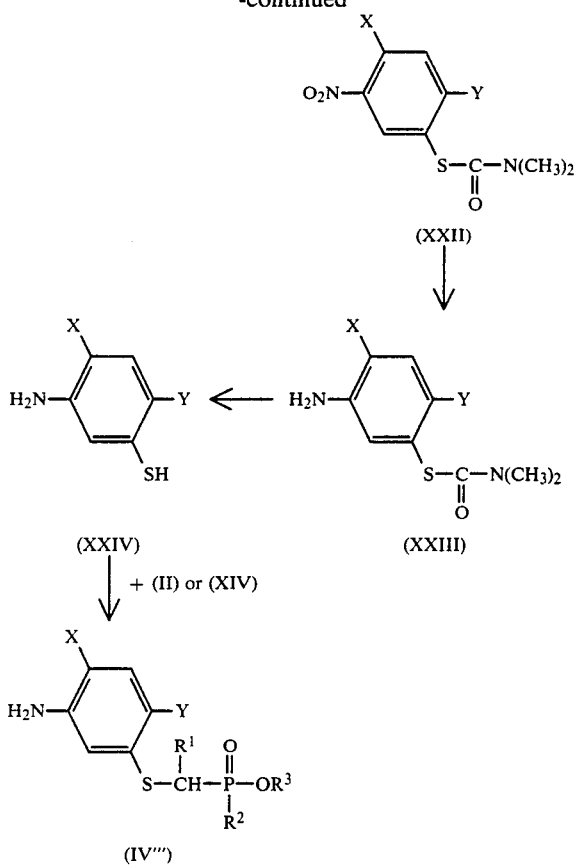

In the above synthesis, a nitrophenol (I) is reacted with dimethylthiocarbamoyl chloride in the presence of 1,4-diazabicyclo(2,2,2-octane) (Dabco) to give the O-nitrophenyldimethylthiocarbamate (XXI), which is then converted to the S-nitrophenylthiocarbamate (XXII) by heating at an elevated temperature, ~230°, following the procedure described by Newman & Karness, *J. Org. Chem.* 31:3980 (1966). The compound (XXII) is hydrogenated to the corresponding S-aminophenylthiocarbamate (XXIII), which is reacted with aqueous sodium hydroxide in a solvent such as methanol or ethanol and at elevated temperature to give an aminophenylthiol (XXIV). The thiols (XXIV) are then reacted with a sulfonate (II) or an alcohol (XIV) following the procedures described hereinabove to give a compound of formula (IV''').

Compounds of formula (A) where M is sulfinyl are prepared by reacting a compound of formula (A) where M is sulfur with one equivalent of sodium periodate or m-chloroperbenzoic acid in a solvent such as methanol or methylene chloride. Compounds where M is sulfonyl are prepared in the same manner, except that two equivalents of m-chloroperbenzoic acid are used. Alternatively, either hydrogen peroxide in warm acetic acid or excess hydrogen peroxide and selenium dioxide is used as the oxidant.

The following terms, wherever used in the description herein and in the appended claims, have the meaning defined below, unless otherwise specified hereinafter.

The term "lower alkyl" refers to an alkyl group, straight or branched, having a chain length of one to eight carbon atoms.

The term "lower alkoxy" refers to an alkoxy group, straight or branched, having a chain length of one to eight carbon atoms.

The term "lower alkenyl" refers to an ethylenically unsaturated hydrocarbon group, straight or branched, having a chain length of two to eight carbon atoms and one or two ethylenic bonds.

The term "cycloalkyl" refers to a cycloalkyl group of three to eight carbon atoms.

The term "alkoxyalkyl" refers to an alkoxyalkyl group of two to eight carbon atoms.

The term "alkoxycarbonylalkyl" refers to an alkoxycarbonylalkyl group of three to nine carbon atoms.

The term "alkylthioalkyl" refers to an alkylthioalkyl group of two to eight carbon atoms.

The term "dialkylaminocarbonylalkyl" refers to a dialkylaminocarbonylalkyl group of four to nine carbon atoms.

The compounds of the present invention have one or more asymmetric carbon atoms. The present invention includes each of the optically active isomers and racemic mixtures thereof. In the examples hereinafter, unless otherwise specified, the compound prepared is a racemic mixture.

The novel compounds of formula (A) are useful for the control of weeds, using pre- and/or post-emergent treatments. The compounds can be applied in the form of dusts, granules, solutions, emulsions, wettable powders, flowables and suspensions. Application of a compound of the present invention is made according to the conventional procedure to the weeds or their locus using an herbicidally effective amount of the compounds, usually from about one-half or less to ten pounds per acre.

Methods of preparing herbicidal formulations which can be used with a compound of the present invention are described in the literature along with suitable liquid and solid carriers, such as in U.S. Pat. Nos. 4,192,669 and 4,163,661, which are incorporated herein by reference. The optimum usage of a compound of the present invention is readily determinable by one of ordinary skill in the art using routine testing such as greenhouse testing and small plot testing.

The term "herbicide," as used herein, refers to an active ingredient which modifies the growth of plants because of phytotoxic or plant growth regulating properties so as to retard the growth of the plant or damage the plant sufficiently to kill it.

While some of the compounds of the present invention have activity on grass weeds, the compounds, in general, demonstrate a higher level of herbicidal activity on broadleaf plants. Broadleaf plant (weed) species on which the compounds of the present invention show effective herbicidal activity include, but are not limited to, mustard, pigweed, velvetleaf, jimsonweed, cocklebur, sicklepod and annual morning glory.

The compounds of the present invention, in view of their broadspectrum broadleaf weed herbicidal activity, can be advantageously combined with grass weed herbicides for broadspectrum postemergence weed control in most grass crops. Examples of herbicides which can be combined with a compound of the present invention include those selected from carbamates, thiocarbamates, chloroacetamides, dinitroanilines, benzoic acids, glycerol ethers, pyridazinones, uracils and ureas for controlling a broad spectrum of weeds.

The following examples are provided to illustrate the practice of the present invention. Temperature is given in degrees Centigrade. "RT" means room temperature.

EXAMPLE 1

A mixture of 2-chloro-4-fluoro-5-aminophenol (0.60 g, 3.72 mmol) in 10 ml of dimethylsulfoxide (DMSO), potassium carbonate (0.62 g, 4.40 mmol) and ethyl P-ethyl(methylsulfonyloxymethyl)phosphinate (1.19 g, 5.21 mmol) is heated to 100° for 48 hours. The reaction mixture is diluted with ether and filtered, and the filtrate is washed with brine, dried and evaporated to dryness. The crude product is purified by preparative thin layer chromatography (prep. TLC) to give ethyl P-ethyl(2-chloro-4-fluoro-5-aminophenoxy)methylphosphinate.

A mixture of the above phosphinate (0.77 g, 2.61 mmol) and 3,4,5,6-tetrahydrophthalic anhydride (0.52 g, 3.39 mmol) in 5 ml of acetic acid is heated under reflux for 9 hours. Excess anhydride and acetic acid are removed in vacuo. The oily product is purified by preparative thin layer chromatography (prep. TLC) to give N-[5-(ethyl P-ethylphosphinomethoxy)-4-chloro-2-fluorophenyl]tetrahydrophthalimide, MS m/e 429 ($M^+$).

The above tetrahydrophthalimide (1.90 g, 4.40 mmol) is dissolved in 20 ml of ether and 10 ml of tetrahydrofuran (THF) and chilled. Hexylamine (0.49 g, 0.64 ml, 4.90 mmol) is added dropwise to the chilled solution, with stirring and the mixture is allowed to warm to RT and stirred, under $N_2$, for 5 hours. The solvent is removed in vacuo. The resulting solid is washed with ether and dried to give N-[4-chloro-2-fluoro-5-(ethyl P-ethylphosphinomethoxy)phenyl]-N'-hexyl-1-cyclohexene-1,2-dicarboxamide, m.p. 129°-130° (compound 1, Table A).

EXAMPLE 2

To a solution of 2,4-dichloro-5-nitrophenol (0.63 g, 3.0 mmol) dissolved in 7 ml of DMSO is added potassium carbonate (0.54 g, 3.9 mmol) and ethyl P-methyl(1-methylsulfonyloxyethyl)phosphinate (0.96 g, 4.2 mmol). The mixture is stirred at 75° under $N_2$ overnight. The reaction is diluted and acidified with 10% HCl and extracted (3X) with methylene chloride. The combined extracts are washed with water (3X), dried over sodium sulfate and evaporated to dryness. The resulting crude product is purified by column chromatography to give ethyl P-methyl[1-(2,4-dichloro-5-nitrophenoxy)ethyl]phosphinate.

Iron metal powder (1.5 g) is added in small portions to a stirring solution of ethyl P-methyl-[1-(2,4-dichloro-5-nitrophenoxy)ethyl]phosphinate (1.00 g, 2.9 mmol) in 5% aqueous acetic acid, and the mixture is heated at 115°-120° for 35 minutes. The reaction mixture is allowed to cool to RT and is made alkyline with potassium carbonate, filtered and extracted with methylene chloride. The combined extracts are washed with water (3X), dried over sodium sulfate and evaporated to dryness to give ethyl P-methyl[1-(2,4-dichloro-5-aminophenoxy)ethyl]phosphinate.

The above aminophenoxyethylphosphinate (0.50 g, 1.6 mmol) is dissolved in glacial acetic acid. 3,4,5,6-Tetrahydrophthalic anhydride (0.29 g, 1.9 mmol) is added to the solution. The mixture is heated at 100° under $N_2$ overnight and then at 140 for an additional 6 hours. It is allowed to cool to RT, adjusted to pH 5–6 with potassium carbonate, diluted with water and extracted with methylene chloride. The extracts are combined, dried over sodium sulfate and evaporated to dryness to give, following purification by prep. TLC, N-[5-((1-ethyl P-methylphosphino)ethoxy))-2,4-dichlorophenyl]tetrahydrophthalimide, MS m/e 446.3 ($M^+$).

Following the procedure of Example 1, the above tetrahydrophthalimide is reacted with hexylamine to give N-[2,4-dichloro-5-((1-(ethyl P-methylphosphino)ethoxy))phenyl]-N'-hexyl-1-cyclohexene-1,2-dicarboxamide (compound 2, Table A).

In the same manner as above, 2-chloro-5-nitrophenol and ethyl P-methyl-(1-methylsulfonyloxyethyl)phosphinate are reacted together and the product is hydrogenated to give ethyl P-methyl-[1-(2-chloro-5-aminophenoxy)ethyl]phosphinate, which is then reacted with hexylamine to yield the final product, N-[4-chloro-5-((1-(ethyl P-methylphosphino)ethoxy))phenyl]-N'-hexyl-1-cyclohexene-1,2-dicarboxamide (compound 3, Table A).

EXAMPLE 3

Following the procedure of Example 1, 2-chloro-4-fluoro-5-aminophenol is reacted with each of the phosphinates under column I, followed by reaction with 3,4,5,6-tetrahydrophthalic anhydride to give the corresponding tetrahydrophthalimide under column II, each of which is then reacted with hexylamine to yield the corresponding phosphinate in Table A.

I 4. methyl P-methyl(methylsulfonyloxymethyl)phosphinate 5. methyl P-ethyl(methylsulfonyloxymethyl)phosphinate 6. ethyl P-methyl(methylsulfonyloxymethyl)phosphinate 7. ethyl P-methyl(1-methylsulfonyloxyethyl)phosphinate 8. ethyl P-ethyl(1-methylsulfonyloxy-n-propyl)phosphinate 9. 2-methoxyethyl P-ethyl(methylsulfonyloxymethyl)phosphinate 10. isopropyl P-ethyl(methylsulfonyloxymethyl)phosphinate

II

4. N-[5-(methyl P-methylphosphinomethoxy)-4-chloro-2-fluorophenyl]tetrahydrophthalimide 5. N-[5-(methyl P-ethylphosphinomethoxy)-4-chloro-2-fluorophenyl]tetrahydrophthalmide 6. N-[5-(ethyl P-methylphosphinomethoxy)-4-chloro-2-fluorophenyl]tetrahydrophthalimide 7. N-[5-((1-(ethyl P-methylphosphino)ethoxy))-4-chloro-2-fluorophenyl]tetrahydrophthalimide, MS m/e 429 ($M^+$)

8. N-[5-((1-(ethyl P-ethylphosphino)-n-propoxy))-4-chloro-2-fluorophenyl]tetrahydrophthalimide, MS m/e 457 ($M^+$)

9. N-[5-(2-methoxyethyl P-ethylphosphinomethoxy)-4-chloro-2-fluorophenyl]tetrahydrophthalimide, MS m/e 459 ($M^+$)

10. N-[5-(isopropyl P-ethylphosphinomethoxy)-4-chloro-2-fluorophenyl]tetrahydrophthalimide, MS m/e 443 ($M^+$)

EXAMPLE 4

Following the procedure of Example 1, N-[5-(ethyl P-ethylphosphinomethoxy)-4-chloro-2-fluorophenyl]-tetrahydrophthalimide is reacted with each of diethylamine, 2-methoxyethylamine, cyclohexylamine and n-butylamine to yield, respectively, N-[4-chloro-2-fluoro-5-(ethyl P-ethylphosphinomethoxy)phenyl]-N',N'-diethyl-1-cyclohexene-1,2-dicarboxamide (compound 11, Table A), N'-[4-chloro-2-fluoro-5-(ethyl P-ethylphosphinomethoxy)phenyl]-N'-2-methoxyethyl-1-cyclohexene-1,2-dicarboxamide (compound 12, Table A), N-[4-chloro-2-fluoro-5-(ethyl P-ethylphosphinomethoxy)phenyl]-N'-cyclohexyl-1-cyclohexene-1,2-dicarboxamide (compound 13, Table A), and N-[4-chloro-2-fluoro-5-(ethyl P-ethylphosphinomethoxy)phenyl]-N'-n-butyl-1-cyclohexene-1,2-dicarboxamide (compound 14, Table A).

EXAMPLE 5

To a solution of 2-chloro-4-fluoro-5-nitrophenol (100 mmol) in DMF (150 ml) is added Dabco (200 mmol) and dimethylthiocarbamoylchloride (150 mmol). The mixture is stirred at 50° for 5 hours, after which it is poured into water, taken up into ether and washed with dilute HCl and with brine. After the product has dried, solvent is removed and the residue is recrystallized to give O-(2-chloro-4-fluoro-5-nitrophenyl)dimethylthiocarbamate. This thiocarbamate is heated at 235° for about one hour to give S-(2-chloro-4-fluoro-5-nitrophenyl)dimethylthiocarbamate.

To a solution of S-(2-chloro-4-fluoro-5-nitrophenyl)-dimethylthiocarbamate (4.20 g, 15.2 mmol) in ethanol (40 ml) and water (20 ml) is added ammonium chloride (0.81 g, 15.2 mmol) and iron (3.00 g, 53.0 mmol). The mixture is heated under reflux for two hours and is then filtered. The filtrate is concentrated to dryness, and the resulting residue is taken up in methylene chloride, washed, dried and evaporated to dryness to give S-(2-chloro-4-fluoro-5-aminophenyl)dimethylthiocarbamate.

The above aminophenylthiocarbamate (3.00 g) is treated with 5% aqueous NaOH (20 ml) in ethanol (20 ml) at reflux temperature overnight. The solvent is removed by evaporation, and the residue is diluted with water. The aqueous solution is neutralized with dilute HCl and the resulting precipitate is collected by filtration and dried to give 2-chloro-4-fluoro-5-aminophenylthiol.

Following the procedure of Example 1, 2-chloro-4-fluoro-5-aminophenylthiol is reacted with ethyl P-ethyl(methylsulfonyloxymethyl)phosphinate to give ethyl P-ethyl(2-chloro-4-fluoro-5-aminophenylthio)methylphosphinate, which is then reacted with 3,4,5,6-tetrahydrophthalic anhydride to yield N-[5-(ethyl P-ethylphosphinomethylthio)-4-chloro-2-fluorophenyl]tetrahydrophthalimide. This tetrahydrophthalimide is then reacted with hexylamine to yield N-[4-chloro-2-fluoro(ethyl-P-ethylphosphinomethylthio)phenyl]-N'-hexyl-1-cyclohexene-1,2-dicarboxamide.

EXAMPLE 6

To a solution of N-[4-chloro-2-fluoro-5-(ethyl P-ethylphosphinomethylthio)phenyl]-N'-hexyl-1-cyclohexene-1,2-dicarboxamide (7.1 mmol) in 10 ml of methanol at 0° is added, dropwise over 5 min., sodium periodate (1.67 g, 7.8 mmol) in 13 ml of water. The mixture is stirred for 3 hours while warming to RT. The reaction is worked up by addition of water and extraction with ether. The combined organic extracts are washed with saturated sodium thiosulfate, with water and with brine, dried and solvent evaporated off to give N-[4-chloro-2-fluoro-5-(ethyl P-ethylphosphinomethylsulfinyl)phenyl]-N'-hexyl-1-cyclohexene-1,2-dicarboxamide.

7.1 Mmol of N-[4-chloro-2-fluoro-5-(ethyl P-ethylmethylthio)phenyl]-N'-hexyl-1-cyclohexene-1,2-dicarboxamide is reacted with 15.6 mmol of m-chloroperbenzoic acid in chloroform to yield N-[4-chloro-2-fluoro-5-(ethyl P-ethylphosphinomethylsulfonyl)phenyl]-N'-hexyl-1-cyclohexene-1,2-dicarboxamide. Alternatively, either hydrogen peroxide in warm acetic acid or excess hydrogen peroxide and selenium dioxide in methanol is used as the oxidant.

EXAMPLE 7

To a mixture of 2-chloro-5-nitroaniline (6.00 g, 34.8 mmol), dimethyl ethylphosphonite (6.4 ml, 6.37 g, 52.2 mmol), and propionaldehyde (7.6 ml, 6.06 g) in toluene (100.0 ml) is added $BF_3$/ether (2.0 ml). The resulting mixture is heated under reflux for 3 hours. After cooling to RT, the reaction mixture is diluted with ether, washed with aqueous sodium bicarbonate and with brine, dried and evaporated to dryness. The residue is purified by prep. TLC to give methyl P-ethyl-1-(2-chloro-5-nitroanilino)propylphosphinate.

A mixture of the above phosphinate (5.06 g, 15.8 mmol), ammonium chloride (0.85 g, 15.8 mmol) and iron (3.53 g, 63.2 mmol) in ethanol (40.0 ml) and water (10.0 ml) is heated under reflux for 4 hours. The reaction mixture is then cooled to RT and filtered, and the filtrate is evaporated to dryness, diluted with methylene chloride, washed with potassium carbonate and aqueous sodium chloride, dried, filtered and evaporated to dryness to give methyl P-ethyl-1-(2-chloro-5-aminoanilino)propylphosphinate.

The above aminoanilinopropylphosphinate (1.41 g, 4.8 mmol) is dissolved in glacial acetic acid (10.0 ml). 3,4,5,6-Tetrahydrophthalic anhydride (1.11 g, 7.3 mmol) is added to the solution, and the mixture is heated under reflux for 16 hours. The acetic acid and excess anhydride are removed in vacuo, and the crude product is purified by prep. TLC to give N-[3-(methyl P-ethylphosphino-1-propylamino)-4-chlorophenyl]tetrahydrophthalimide.

The above tetrahydrophthalimide is dissolved in a mixture of ether (20 ml) and THF (10 ml). To this is added hexylamine (0.43 ml, 0.33 g, 3.3 mmol) at 5° and with stirring under $N_2$. The mixture is slowly warmed to RT and stirred at RT for 5 hours. The solvent is evaporated off to give, after purification by prep. TLC, N-[4-chloro-3-((1-methyl P-ethylphosphino)-propylamino))phenyl]-N'-hexyl-1-cyclohexene-1,2-dicarboxamide, light grey crystals, m.p. 131°–133° (compound 1, Table B).

EXAMPLE 8

Following the procedure of Example 7, N-[3-(methyl P-ethylphosphino-1-propylamino)-4-chlorophenyl]tetrahydrophthalimide (0.76 g, 1.8 mmol) and n-butylamine are reacted together to give N-[4-chloro-3-((1-(methyl P-ethylphosphino)propylamino))-phenyl]-N'-n-butyl-1-cyclohexene-1,2-dicarboxamide a yellow solid, MS m/e 498 (M+) (compound 2, Table B).

In the same manner, N-[3-(methyl P-ethylphosphino-1-propylamino)-4-chlorophenyl]tetrahydrophthalimide is reacted with each of diethylamine, 2-methoxyethylamine and cyclohexylamine to yield, respectively, N-[4-chloro-3-((1-(methyl P-ethylphosphino)-propylamino))phenyl]-N',N'-diethyl-1-cyclohexene-1,2-dicarboxamide (compound 3, Table B), N-[4-chloro-3-((1-(methyl P-ethylphosphino)-propylamino))phenyl]-N'-2-methoxyethyl-1-cyclohexene-1,2-dicarboxamide (compound 4, Table B), and N-[4-chloro-3-((1-(methyl P-ethylphosphino)-propylamino))phenyl]-N'-cyclohexyl-1-cyclohexene-1,2-dicarboxamide (compound 5, Table B).

EXAMPLE 9

Following the procedure of Example 7, 2-chloro-5-nitroaniline, dimethyl ethylphosphonite and p-formaldehyde are reacted together and the resulting nitro compound is hydrogenated to give methyl P-ethyl(2-chloro-5-aminoanilino)methylphosphinate, which is then reacted with 3,4,5,6-tetrahydrophthalic anhydride to give N-[3-(methyl P-ethylphosphinomethylamino)-4-chlorophenyl]tetrahydrophthalimide. This tetrahydrophthalimide is reacted with hexylamino to yield N-[4-chloro-3-(methyl P-ethylphosphinomethylamino)-phenyl]-N'-hexyl-1-cyclohexene-1,2-dicarboxamide (compound 6, Table B).

In the same manner, each of 2,4-dichloro-5-nitroaniline and 2-chloro-4-fluoro-5-nitroaniline is reacted with dimethyl ethylphosphonite and p-formaldehyde. The resulting phosphinates are hydrogenated to the corresponding amino compounds, which are each reacted with 3,4,5,6-tetrahydrophthalic anhydride to give, respectively, N-[3-(methyl P-ethylphosphinomethylamino)-2,4-dichlorophenyl]tetrahydrophthalimide and N-[5-(methyl P-ethylphosphinomethylamino)-4-chloro-2-fluorophenyl]tetrahydrophthalimide. Each of the tetrahydrophthalimides is then reacted with hexylamine to yield, respectively, N-[2,4-dichloro-3-(methyl P-ethylphosphinomethylaminophenyl]-N'-hexyl-1-cyclohexene-1,2-dicarboxamide (compound 7, Table B) and N-[4-chloro-2-fluoro-5-(methyl P-ethylphosphinomethylamino)phenyl]-N'-hexyl-1-cyclohexene-1,2-dicarboxamide (compound 8, Table B).

EXAMPLE 10

Following the procedure of Example 7, 2-chloro-5-nitroaniline, dimethyl ethylphosphonite and acetaldehyde are reacted together and the resulting phosphinate is hydrogenated to methyl P-ethyl-1-(2-chloro-5-aminoanilino)ethylphosphinate, which is reacted with 3,4,5,6-tetrahydrophthalic anhydride to given N-[3-(methyl P-ethylphosphino-1-ethylamino)-4-chlorophenyl]tetrahydrophthalimide. This tetrahydrophthalimide is reacted with hexylamine to give N-[4-chloro-3-((1-(methyl P-ethylphosphino)ethylamino))phenyl]-N'-hexyl-1-cyclohexene-1,2-dicarboxamide (compound 9, Table B).

EXAMPLE 11

Following the procedure of Example 7, 2-chloro-5-nitroaniline and p-formaldehyde are reacted with each of the phosphonites under column III. Each of the resulting nitroanilinomethylphosphinates is hydrogenated to the corresponding amino compound, which is reacted with 3,4,5,6-tetrahydrophthalic anhydride to give the corresponding tetrahydrophthalimide under column IV. Each of these is reacted with hexylamine to give the corresponding phosphinate in Table B.

III 10. diethyl ethylphosphonite
11. dimethyl isopropylphosphonite
12. dimethyl n-propylphosphonite
13. dimethyl methylphosphonite

IV

10. N-[3-(ethyl P-ethylphosphinomethylamino)-4-chlorophenyl]tetrahydrophthalimide
11. N-[3-(methyl P-isopropylphosphinomethylamino)-4-chlorophenyl]tetrahydrophthalimide
12. N-[3-(methyl P-n-propylphosphinomethylamino)-4-chlorophenyl]tetrahydrophthalimide
13. N-[3-(methyl P-methylphosphinomethylamino)-4-chlorophenyl]tetrahydrophthalimide

EXAMPLE 12

Thionyl chloride (8 ml) is added to methyl P-ethyl-2-chloro-5-nitroanilinomethylphosphinate, and the mixture is allowed to stand at RT overnight. The excess thionyl chloride is then removed to give P-ethyl-2-chloro-5-nitroanilinomethylphosphinic acid chloride. The acid chloride is treated with 2.0 g of sodium hydroxide in water (100 ml). The aqueous solution is acidified and extracted with ether, and the combined ether extracts are dried and evaporated to dryness to give P-ethyl-2-chloro-5-nitroanilinomethylphosphinic acid.

A mixtue of the above phosphinic acid (5.59 mmol), potassium carbonate (0.9 g), methyl bromoacetate (1.2 g, 0.74 ml, 7.80 mmol) and acetone (20 ml) is heated under reflux overnight. The reaction mixture is allowed to cool to RT and filtered, and the filtrate is concentrated. The residue is extracted in methylene chloride and the combined extracts are washed, dried and evaporated to dryness to give methoxycarbonylmethyl P-ethyl-2-chloro-5-nitroanilinomethylphosphinate.

The above phosphinate is suspended in 5% acetic acid (50 ml) and iron powder (2.0 g) is added. The mixture is heated under reflux for one hour. After cooling to RT, the reaction mixture is filtered, and the filtrate is extracted with methylene chloride. The combined extracts are dried over magnesium sulfate and concentrated to dryness to give, after purification by prep. TLC, methoxycarbonylmethyl P-ethyl-2-chloro-5-aminoanilinomethylphosphinate.

The above aminoanilino phosphinate (4.10 mmol), 3,4,5,6-tetrahydrophthalic anhydride (0.75 g, 4.90 mmol) and acetic acid (4 ml) are mixed together and heated under reflux for about 6 hours. The solution is concentrated to dryness and any excess starting anhydride is removed in vacuo. The crude product is purified by prep. TLC to give N-[3-(methoxycarbonylmethyl P-ethylphosphinomethylamino)-4-chlorophenyl]tetrahydrophthalimide.

Following the procedure of Example 1, the above tetrahydrophthalmide is reacted with hexylamine to give N-[4-chloro-3-(methoxycarbonylmethyl P-ethylphosphinomethylamino)phenyl]-N'-hexyl-1-cyclohexene-1,2-dicarboxamide (compound 14, Table B).

TABLE A

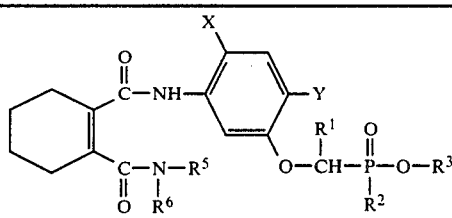

| Compound | X  | Y  | $R^1$      | $R^2$      | $R^3$       | $R^5$      | $R^6$          |
|----------|----|----|------------|------------|-------------|------------|----------------|
| 1        | F  | Cl | H          | $CH_2CH_3$ | $CH_2CH_3$  | H          | $CH_2(CH_2)_4CH_3$ |
| 2        | Cl | Cl | $CH_3$     | $CH_3$     | $CH_2CH_3$  | H          | $CH_2(CH_2)_4CH_3$ |
| 3        | H  | Cl | $CH_3$     | $CH_3$     | $CH_2CH_3$  | H          | $CH_2(CH_2)_4CH_3$ |
| 4        | F  | Cl | H          | $CH_3$     | $CH_3$      | H          | $CH_2(CH_2)_4CH_3$ |
| 5        | F  | Cl | H          | $CH_3CH_2$ | $CH_3$      | H          | $CH_2(CH_2)_4CH_3$ |
| 6        | F  | Cl | H          | $CH_3$     | $CH_2CH_3$  | H          | $CH_2(CH_2)_4CH_3$ |
| 7        | F  | Cl | $CH_3$     | $CH_3$     | $CH_2CH_3$  | H          | $CH_2(CH_2)_4CH_3$ |
| 8        | F  | Cl | $CH_2CH_3$ | $CH_2CH_3$ | $CH_2CH_3$  | H          | $CH_2(CH_2)_4CH_3$ |
| 9        | F  | Cl | H          | $CH_2CH_3$ | $CH_2CH_2OCH_3$ | H      | $CH_2(CH_2)_4CH_3$ |
| 10       | F  | Cl | H          | $CH_2CH_3$ | $CH(CH_3)_2$ | H         | $CH_2(CH_2)_4CH_3$ |
| 11       | F  | Cl | H          | $CH_2CH_3$ | $CH_2CH_3$  | $CH_2CH_3$ | $CH_2CH_3$     |
| 12       | F  | Cl | H          | $CH_2CH_3$ | $CH_2CH_3$  | H          | $CH_2CH_2OCH_3$ |
| 13       | F  | Cl | H          | $CH_2CH_3$ | $CH_2CH_3$  | H          | $C_6H_{11}$    |
| 14       | F  | Cl | H          | $CH_2CH_3$ | $CH_2CH_3$  | H          | $CH_2(CH_2)_2CH_3$ |

TABLE B

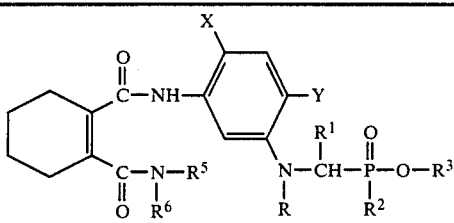

| Compound | X  | Y  | R | $R^1$      | $R^2$          | $R^3$       | $R^5$      | $R^6$              |
|----------|----|----|---|------------|----------------|-------------|------------|--------------------|
| 1        | H  | Cl | H | $CH_2CH_3$ | $CH_2CH_3$     | $CH_3$      | H          | $CH_2(CH_2)_4CH_3$ |
| 2        | H  | Cl | H | $CH_2CH_3$ | $CH_2CH_3$     | $CH_3$      | H          | $CH_2(CH_2)_2CH_3$ |
| 3        | H  | Cl | H | $CH_2CH_3$ | $CH_2CH_3$     | $CH_3$      | $CH_2CH_3$ | $CH_2CH_3$         |
| 4        | H  | Cl | H | $CH_2CH_3$ | $CH_2CH_3$     | $CH_3$      | H          | $CH_2CH_2OCH_3$    |
| 5        | H  | Cl | H | $CH_2CH_3$ | $CH_2CH_3$     | $CH_3$      | H          | $C_6H_{11}$        |
| 6        | H  | Cl | H | H          | $CH_2CH_3$     | $CH_3$      | H          | $CH_2(CH_2)_4CH_3$ |
| 7        | Cl | Cl | H | H          | $CH_2CH_3$     | $CH_3$      | H          | $CH_2(CH_2)_4CH_3$ |
| 8        | F  | Cl | H | H          | $CH_2CH_3$     | $CH_3$      | H          | $CH_2(CH_2)_4CH_3$ |
| 9        | H  | Cl | H | $CH_3$     | $CH_2CH_3$     | $CH_3$      | H          | $CH_2(CH_2)_4CH_3$ |
| 10       | H  | Cl | H | H          | $CH_2CH_3$     | $CH_2CH_3$  | H          | $CH_2(CH_2)_4CH_3$ |
| 11       | H  | Cl | H | H          | $CH(CH_3)_2$   | $CH_3$      | H          | $CH_2(CH_2)_4CH_3$ |
| 12       | H  | Cl | H | H          | $CH_2CH_2CH_3$ | $CH_3$      | H          | $CH_2(CH_2)_4CH_3$ |
| 13       | H  | Cl | H | H          | $CH_3$         | $CH_3$      | H          | $CH_2(CH_2)_4CH_3$ |
| 14       | H  | Cl | H | H          | $CH_2CH_3$     | $CH_2C(O)OCH_3$ | H      | $CH_2(CH_2)_4CH_3$ |

What is claimed is:

1. A compound of the following formula (A):

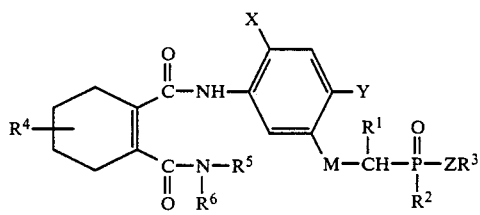

(A)

wherein,

M is oxygen, sulfur, sulfinyl, sulfonyl or N—R;

each of X and Y is independently hydrogen or halogen;

Z is oxygen;

each of R and $R^1$ is independently hydrogen or lower alkyl;

$R^2$ is lower alkyl;

$R^3$ is lower alkyl, alkoxyalkyl or alkoxycarbonylalkyl;

$R^4$ is hydrogen;

$R^5$ is lower alkyl, cycloalkyl or alkoxyalkyl; and $R^6$ is hydrogen or lower alkyl.

2. A compound of according to claim 1 wherein M is N—R, $R^4$ is hydrogen and Z is oxygen.

3. A compound according to claim 2 wherein R is hydrogen; $R^1$ is hydrogen, methyl or ethyl; $R^2$ is lower alkyl; and $R^3$ is lower alkyl or alkoxycarbonylalkyl.

4. A compound according to claim 3 wherein X is hydrogen, chloro or fluoro and Y is chloro.

5. A compound according to claim 4 wherein $R^5$ is hydrogen and $R^6$ is lower alkyl.

6. A compound according to claim 5 wherein $R^2$ is methyl or ethyl and $R^3$ is methyl or ethyl.

7. A compound according to claim 6 wherein $R^6$ is hexyl.

8. A compound according to claim 1 wherein M is oxygen, $R^4$ is hydrogen and Z is oxygen.

9. A compound according to claim 8 wherein $R^1$ is hydrogen, methyl or ethyl; $R^2$ is lower alkyl; and $R^3$ is lower alkyl or alkoxycarbonylalkyl.

10. A compound according to claim 9 wherein X is chloro or fluoro and Y is chloro.

11. A compound according to claim 10 wherein $R^5$ is hydrogen and $R^6$ is lower alkyl.

12. A compound according to claim 11 wherein $R^2$ is methyl or ethyl and $R^3$ is methyl or ethyl.

13. A compound according to claim 12 wherein $R^6$ is hexyl.

* * * * *